(12) United States Patent
Toumazou et al.

(10) Patent No.: US 9,140,663 B2
(45) Date of Patent: Sep. 22, 2015

(54) ISFET SWITCH

(75) Inventors: Christofer Toumazou, London (GB); Abdulrahman Al-Ahdal, London (GB)

(73) Assignee: DNA ELECTRONICS LIMITED, London (GB)

( * ) Notice: Subject to any disclaimer, the term of this patent is extended or adjusted under 35 U.S.C. 154(b) by 148 days.

(21) Appl. No.: 13/878,402

(22) PCT Filed: Oct. 10, 2011

(86) PCT No.: PCT/IB2011/002376
§ 371 (c)(1),
(2), (4) Date: Jun. 11, 2013

(87) PCT Pub. No.: WO2012/046137
PCT Pub. Date: Apr. 12, 2012

(65) Prior Publication Data
US 2013/0273664 A1    Oct. 17, 2013

(30) Foreign Application Priority Data
Oct. 8, 2010 (GB) .................................... 1017023.1

(51) Int. Cl.
*G01N 27/414* (2006.01)
*G11C 16/04* (2006.01)

(52) U.S. Cl.
CPC .......... *G01N 27/4148* (2013.01); *G11C 16/045* (2013.01); *G11C 16/0416* (2013.01); *G11C 16/0441* (2013.01); *Y10T 436/143333* (2015.01)

(58) Field of Classification Search
CPC ........... G01N 27/4148; G11C 16/0416; G11C 16/0441; G11C 16/045; Y10T 436/143333

USPC ......... 436/94, 149, 150, 151, 163; 422/82.01, 422/82.02, 82.03; 257/213, 253
See application file for complete search history.

(56) References Cited

U.S. PATENT DOCUMENTS

2005/0230271 A1* 10/2005 Levon et al. .................. 205/789
2010/0159461 A1* 6/2010 Toumazou et al. ............... 435/6

OTHER PUBLICATIONS

International Search Report dated Mar. 23, 2012, as issued in corresponding International Patent Application No. PCT/IB2011/002376—2 pages.
Nishiguchi Katsuhiko, et al., "Si nanowire ion-sensitive field-effect transistors with a shared floating gate", Applied Physics Letters, AIP, American Institute of Physics., vol. 94, No. 16, pp. 163106;1-163106;3, Apr. 21, 2009.
Wai Pan Chan, et al., "An Integrated ISFETs Instrumentation System in Standard CMOS Technology", IEEE Journal of Solid-State Circuits, IEEE Service Center, vol. 45, No. 9, pp. 1923-1934, Sep. 1, 2010.
Pantelis Georgiou, et al., "Spiking Chemical Sensor (SCS): A new platform for neuro-chemical sensing", 2007 3rd International IEEE/EMBS Conference on Neural Engineering, pp. 126-129, May 1, 2007.

(Continued)

*Primary Examiner* — Maureen Wallenhorst
(74) *Attorney, Agent, or Firm* — Maier & Maier, PLLC

(57) ABSTRACT

There is provided a semiconductor device for detecting a change in ion concentration of a sample and method of using same. The device can have a plurality of Field Effect Transistors (FETs) coupled to a common floating gate and an ion sensing layer exposed to the sample and coupled to the floating gate. There may be other input voltages coupled to the floating gate.

24 Claims, 12 Drawing Sheets

(56) References Cited

OTHER PUBLICATIONS

D. Ali, et al., "Design of a Single-Chip pH Sensor Using a Conventional 06-mu.m CMOS Process", IEEE Senors Journal, IEEE Service Center, vol. 4, No. 6, pp. 706-712, Dec. 1, 2004.

Paul A. Hammond, et al., "Design of a Single-Chip pH Sensor Using a Conventoinal 06-μm CMOS Process", Sensors Journal, vol. 4, No. 6, Dec. 2004, pp. 706-712.

* cited by examiner

ISFET SWITCH

RELATED APPLICATIONS

This is the U.S. national stage application which claims priority under 35 U.S.C. §371 to International Patent Application No. PCT/IB2011/002376 filed on Oct. 10, 2011, which claims priority to Great Britain Patent Application No. 1017023.1 filed on Oct. 8, 2010, the disclosures of which are incorporated by to reference herein their entireties.

FIELD OF THE INVENTION

The present invention relates to a device and method for switching an electrical output according to the ion concentration of a sample.

BACKGROUND

Generally ISFETs were built for continuous time (analogue) measurement with analogue pre-processing circuits around them. Normally analogue to digital conversion is one of the processing steps. This is the case where a continuum of values is needed. However, there are many applications where a yes/no decision is sought. For example, in DNA hybridization and SNP insertion detection, it is enough to detect that a process took place or not with a yes/no answer (5) (6). Other applications require just comparison between concentrations of two chemicals in a solution. For example, if Creatinine is of higher concentration than Urea or vice versa (7).

An Ion Sensitive Field Effective Transistor (ISFET) is comprised of a Field Effect Transistor (FET) whose gate is exposed to ionic charges in a electrolyte. A reference electrode is immersed in the electrolyte solution which comes into contact with the gate oxide of the transistor. See FIG. 1. Therefore, the combination of the electrolyte and the reference electrode plays the role of the gate in a normal MOSFET. The gate oxide becomes the ions sensitive membrane. The electrical operating modes of a FET may be expressed by:

Weak inversion $$I_{DS} = I_{D0} \frac{W}{L} e^{\left(\frac{V_{GS}-V_t}{nU_T}\right)}$$

Triode Region   Saturation                                  (1)

$$I_{DS} = \mu C_{ox} \frac{W}{L} \left( (V_{gs} - V_t)V_{DS} - \frac{V_{DS}^2}{2} \right)$$

$$I_{DS} = \frac{1}{2} \mu C_{ox} \frac{W}{L} (V_{GS} - V_t)^2 (1 + \lambda V_{DS})$$

The voltage drops arising from interactions of the reference electrode, the electrolyte and the ion sensitive membrane can be viewed as part of either the gate-source voltage ($V_{gs}$) or the threshold voltage ($V_t$). This is supported by the fact that it is their difference that appears in the MOSFET $I_d$-$V_{gs}$ relations in all regions of operation, equation (1).

From the above analogy, it was debated whether the reference electrode remotely plays the role of the MOS gate (1). Therefore, the electrolyte plays the role of the gate metal which comes into contact with the gate-oxide. In MOSFET, $V_t$ is decided by the gate material, substrate doping, their insulator and the charges in this system, equation (2). It is a constant for each device; and because the manufacturing process is very well controlled, its variation across devices is well controlled. However, in the ISFET according to this analogy, the electrolyte became part of this system making its $V_t$ dependant on the electrolyte properties, equation (3) (1). The threshold voltage may be expressed by:

$$MOSFET\ V_t = \frac{\Phi_M - \Phi_{Si}}{q} - \frac{Q_{ox} + Q_{ss} + Q_B}{C_{ox}} + 2\phi_f \quad (2)$$

$$ISFET\ V_t = -\Psi + \chi^{sol} - \frac{\Phi_{Si}}{q} - \frac{Q_{ox} + Q_{ss} + Q_B}{C_{ox}} + 2\phi_f \quad (3)$$

Where: $\phi_M$ is the metal work function, $\phi_{Si}$ is the Silicon work function, q is the electron charge, Qox is accumulated charges in the oxide insulator, Qss is trapped charge in the oxide-Silicon interface, QB is depletion charge in the silicon bulk, Cox is gate oxide capacitance, and $\phi_f$ defines the onset of inversion depending on silicon doping levels. In equation (3), $\phi_M$ is replaced by both the chemical parameter of the ion sensitive membrane-electrolyte interface potential $\Psi$, and the surface dipole potential of the electrolyte in contact with the ion sensitive membrane $\chi^{sol}$. The former is a function of the electrolyte ion concentration, where pH is a possible measure of it. The latter is a constant. Equation (3) suggests that the ISFET's threshold voltage can be modified using electrolyte ion concentration (1).

In 1999, Bausells et al integrated an ISFET using the 1 µm single poly-silicon, double metal standard CMOS process of Atmel-ES2 (10). They integrated a standard CMOS amplifier in the same die. Basically, the ISFET was given, for the first time, a poly-silicon gate that was floating and connected to the metal stack until the topmost metal layer where the ions were sensed through the oxi-nitride passivation. This basic idea was carried out by others and ISFETs were built in different commercial CMOS processes with multiple metal layers (10) (11) (12).

It is interesting to note that the transistor part here is effectively an FG-MOSFET and the sensitive part looks like an ion sensitive capacitor where the topmost metal is one plate and the electrolyte forms the second while passivation is the insulation layer. This is very similar to the traditional capacitive ion sensor which results if the reference electrode is removed.

The passivation capacitance from the transistor's gate may be considered split to make two different structures. Hence, the ISFET's transistor gate may be called the "electrical gate" and the topmost metal under the ion sensitive membrane may be called the "chemical gate".

Therefore, $V_t$ is a process dependant constant given by equation (2). The chemical dependence introduced into equation (3) may be expressed as part of the floating gate voltage of the ISFET given by:

$$V_{FC} = V_{ref} \Psi + \chi^{sol} + V_{Qpass} \quad (4)$$

Where, $V_{Qpass}$ is due to the trapped charges in the passivation layer.

Using the site-dissociation model and the Gouy-Chapman-Stern double layer model, the ISFET may be modeled as in FIG. 2. Where $V_{chem}$ is the chemical voltage arising from the electrolyte and its interface to both reference electrode and ion sensing membrane (6).

$$V_{chem} = \gamma + V_{Qpass} + 2.3\alpha U_T pH \quad (5)$$

Where, $\gamma$ is a grouping of all pH independent terms apart from passivation trapped charges which is $V_{Qpass}$. $U_T$ is the usual thermal voltage, and $\alpha$ is a sensitivity parameter with values between $0<\alpha<1$. Its maximum gives the theoretical limit known as the Nernstian sensitivity given by 59.2 mV/pH at 25° C. (1).

Most of the publications about ISFETs consider $V_t$ as the pH dependant parameter. The inventors have appreciated that from a pure circuit point of view, the ISFET is effectively a standard FGMOS with its gate capacitively coupled to the superimposed voltages $V_{ref}$ and $V_{chem}$. Therefore, they considered them to form the floating gate input and assume $V_t$ as a constant, like a standard MOSFET. Thus a pH change is can be seen as a modulation for $V_{gs}$ instead of $V_t$. However, from a physical point of view, there is no change to the system and the same analysis holds. Therefore, equations (1) and (2) are still valid, equation (3) is no more relevant, and equation (5) represents the chemical voltage.

The first attempt to use an ISFET to build an inverter was by Dr. Shepherd and her colleagues (5) (16). FIG. 4 shows an ISFET as an NMOS in a standard class AB inverting amplifier with the PMOS role taken by a normal transistor. The input is connected to both the gate of the PMOS (M2) and the reference electrode of the n-ISFET (X1). Therefore, the switching threshold of the circuit shifts in proportion to the solution's pH.

Therefore pH changes modulate the gate voltage of the n-MOS but not the p-MOS. That is, only half of the complementary pair is pH sensitive. The pull up transistor sees a different input than the pull down transistor, the difference being $V_{chem}$.

However, this may be acceptable if there is no drift or passivation trapped charges. An ISFET's $V_t$ can have an initial variation, due to passivation trapped charges, in the range of few Volts (17) (12). This can render the switching function of that circuit non-operational, especially if the n-ISFET had a negative threshold voltage.

SUMMARY OF THE INVENTION

According to the first aspect of the invention there is provided a semiconductor device for detecting a change in ion concentration of a sample, the device comprising a plurality of Field Effect Transistors (FETs) coupled to a common floating gate and an ion sensing layer exposed to the sample and coupled to the floating gate.

In use, a current through the transistors is switched on or off depending on the magnitude of the ion concentration in the sample in proximity to the sensing layer compared to a switching threshold.

The device may be build using commercial CMOS processes.

According to the second aspect of the invention there is provided a device for detecting a ion concentration of a sample, the device comprising a Field Effect Transistor (FET) coupled to a floating gate, an ion sensing layer exposed to the sample and coupled to the floating gate and one or more electrical input signals coupled to the floating gate for removing or adding a charge to the floating gate to set a switching threshold for the plurality of transistors.

The electrical input signals may be arranged to be coupled to the floating gate to set the switching threshold and de-coupled when not setting the switching threshold. According to the third aspect of the invention there is provided a device for detecting a ion concentration of a sample, the device comprising a Field Effect Transistor (FET) coupled to a floating gate, an ion sensing layer exposed to the sample and coupled to the floating gate, and an electrical input signal coupled to the floating gate, wherein the electrical input signal is arranged to change in magnitude so as to switch the plurality of Field Effect Transistors.

According to the fourth aspect of the invention there is provided a circuit for detecting a plurality of chemical reactions and evaluating a logical function having the result of each of the plurality of chemical reactions as its inputs, the circuit comprising at least one reaction chamber for each of the plurality of chemical reactions, which chemical reactions change an ion concentration in the reaction chamber. Each reaction chamber is provided with an device according to the first aspect, each device providing a digital output signal whose state depends on the ion concentration of that chamber, and wherein the outputs are coupled together to form a digital signal processing circuit for evaluating a logical function.

According to the fifth aspect of the invention there is provided a method of providing an output representing a concentration of a target ion in a sample. The method comprises providing a CMOS switch comprising a plurality of Field Effect Transistors (FETs) coupled to a common floating gate and an ion sensing layer exposed to the sample and coupled to the floating gate; exposing the ion sensitive layer to the sample to switch a state of the CMOS switch on or off; and outputting a signal from the CMOS switch.

By using a common floating gate, the device can switch with high sensitivity to ionic changes, and lower sensitivity to other components like trapped charge.

By modifying known inverter circuits, the inventors have increased the sensitivity by orders of magnitudes. High sensitivity pH driven inverters make it possible to detect small pH changes that would not otherwise be feasible. This enhances measurement sensitivities and relaxes constraints on sample volumes and concentrations.

This circuit can be used to perform reaction monitoring and pH-thresholding operations for a reaction chamber. Its digital output can be used to build standard digital circuits with inputs coming from different reaction champers. This facilitates the construction of completely digital ISFET based lab on chip applications.

BRIEF DESCRIPTION OF THE DRAWINGS

Specific embodiments of the invention will now be described by way of example only with reference to the accompanying figures, in which.

DETAILED DESCRIPTION

In discussions below, an ISFET may be viewed as a FET capacitively coupled to a chemical signal. The transistor part may be dealt with as a normal FGMOS. The system comprises a reference electrode, electrolyte, sensing membrane and the metal underneath collectively form one entity that may be called an Ion Sensitive Capacitor (ISCAP).

With this point of view, a traditional ISFET is basically one ISCAP as the only input to one FGMOS. However, in general, one or more ISCAPs are possible inputs to a network of floating gates of an n-number of FGMOS transistors. A number of other capacitively coupled inputs are also possible as shown by Vin1 and Vin2 in FIG. 5.

The floating gate voltage may be expressed as a weighted sum of the voltages that are capacitively coupled to it. That is:

$$V_{FG} = \frac{(V_{ref1} + V_{chem1})C_{s1}}{C_{tot}} + \frac{(V_{ref2} + V_{chem2})C_{s2}}{C_{tot}} + \frac{V_{in1}C_1}{C_{tot}} + \frac{V_{in2}C_2}{C_{tot}} + \frac{V_{sub1}C_{g1}}{C_{tot}} + \frac{V_{sub2}C_{g2}}{C_{tot}} \quad (6)$$

$C_{g1}$ and $C_{g2}$ are the gate oxide capacitances of the two transistors in the figure. They can be a good approximation of the transistors' capacitances if they are in inversion and a channel is formed. For simplicity, they are assumed constant and the gate sizes are large enough to supersede the parasitic capacitances.

Figure 1:
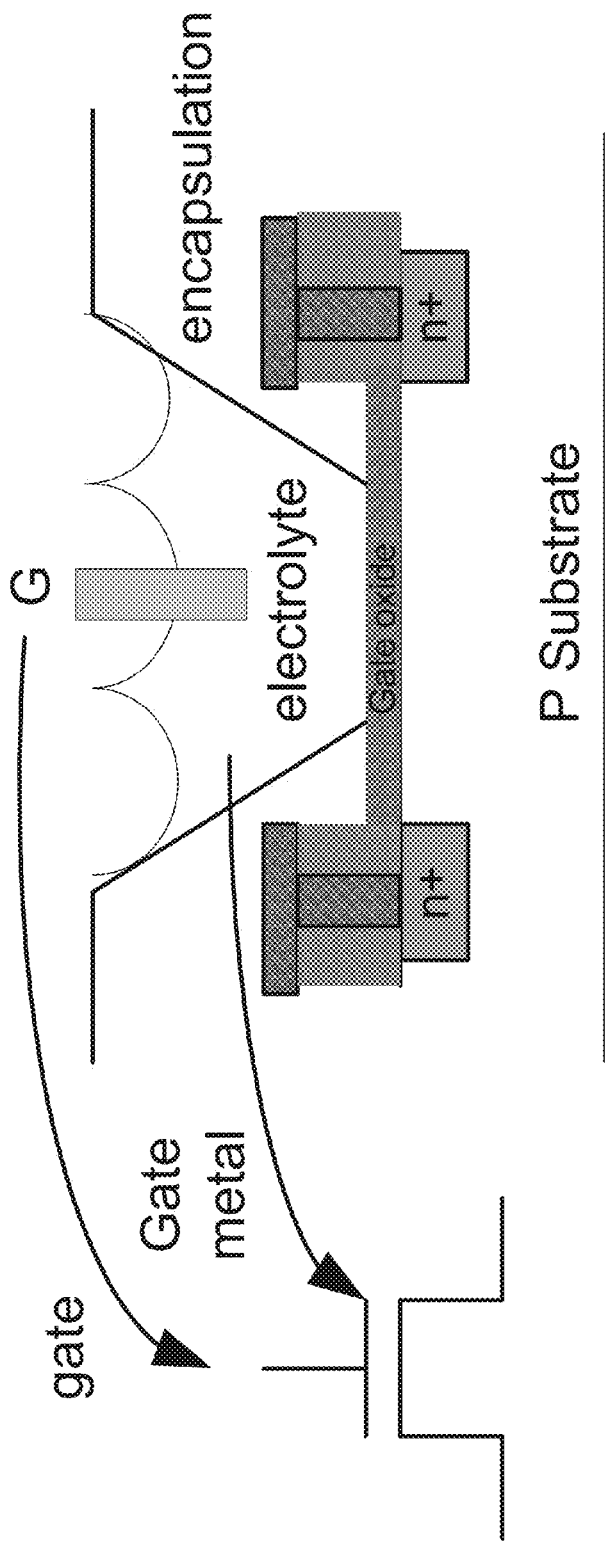
FIG. 1 is a cross-section illustration of an ISFET and analogy to MOSFET.
Figure 2:
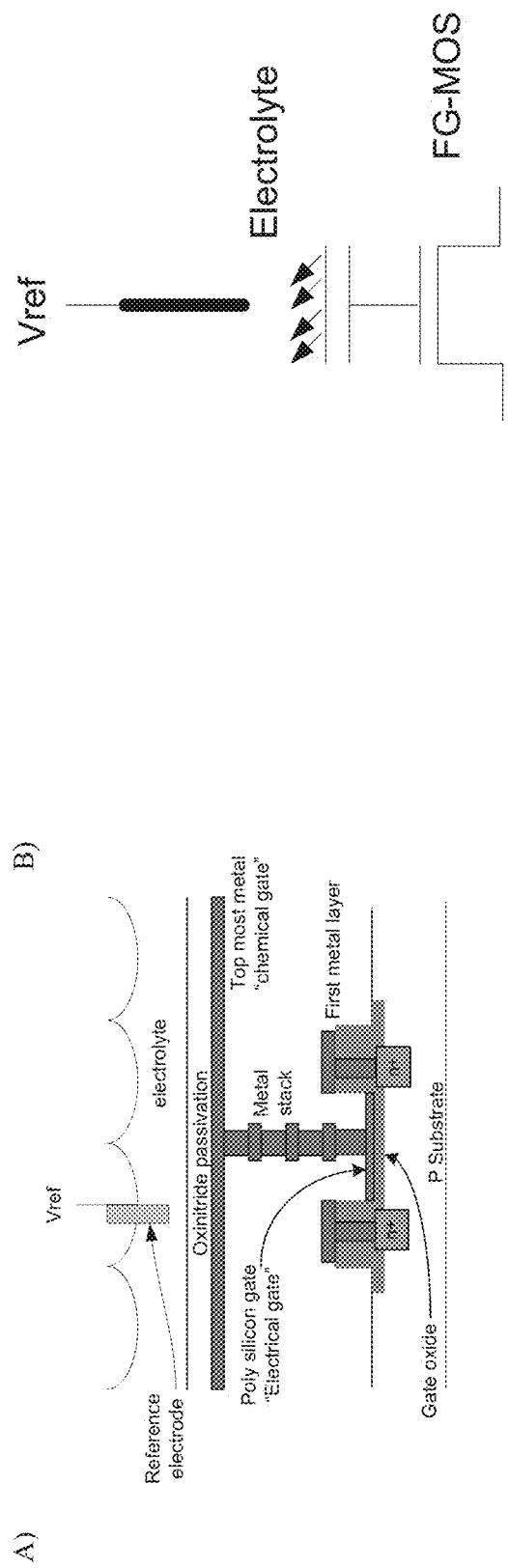
FIG. 2 is (A) a Cross section representation of an ISFET built in a standard CMOS process and, (B) its circuit representation.
Figure 3:
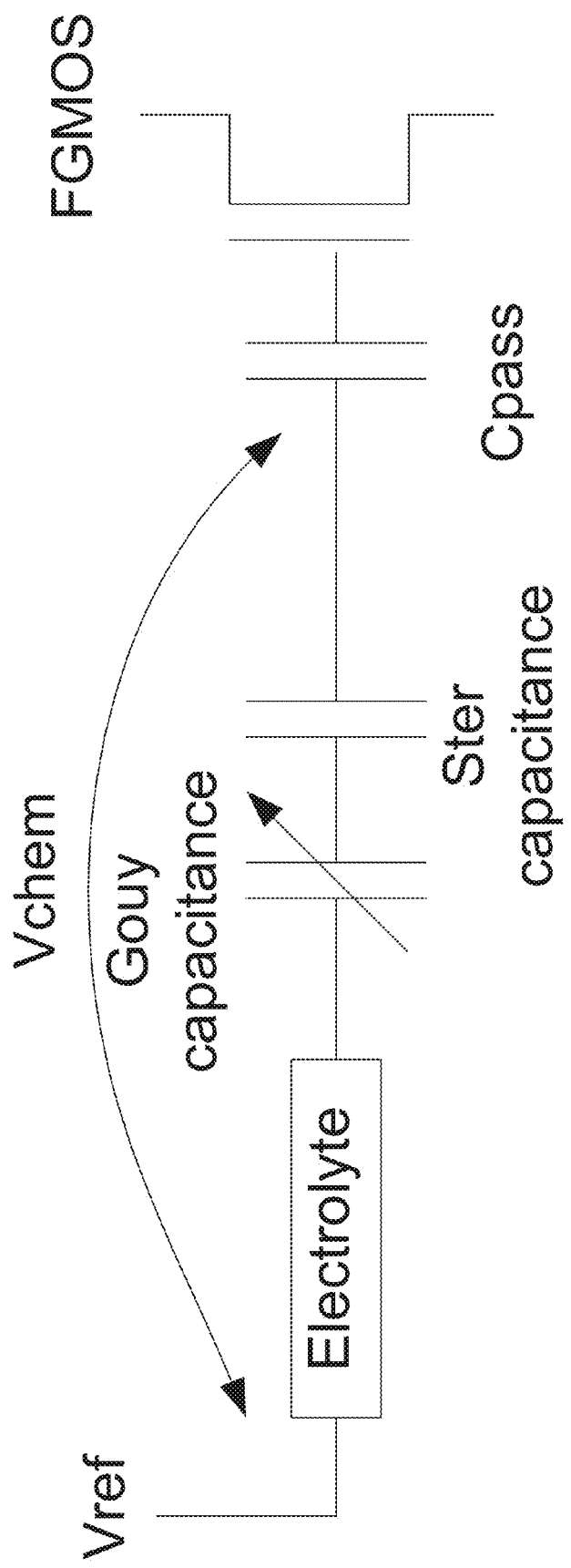
FIG. 3 is a model of an ISFET.
Figure 4:
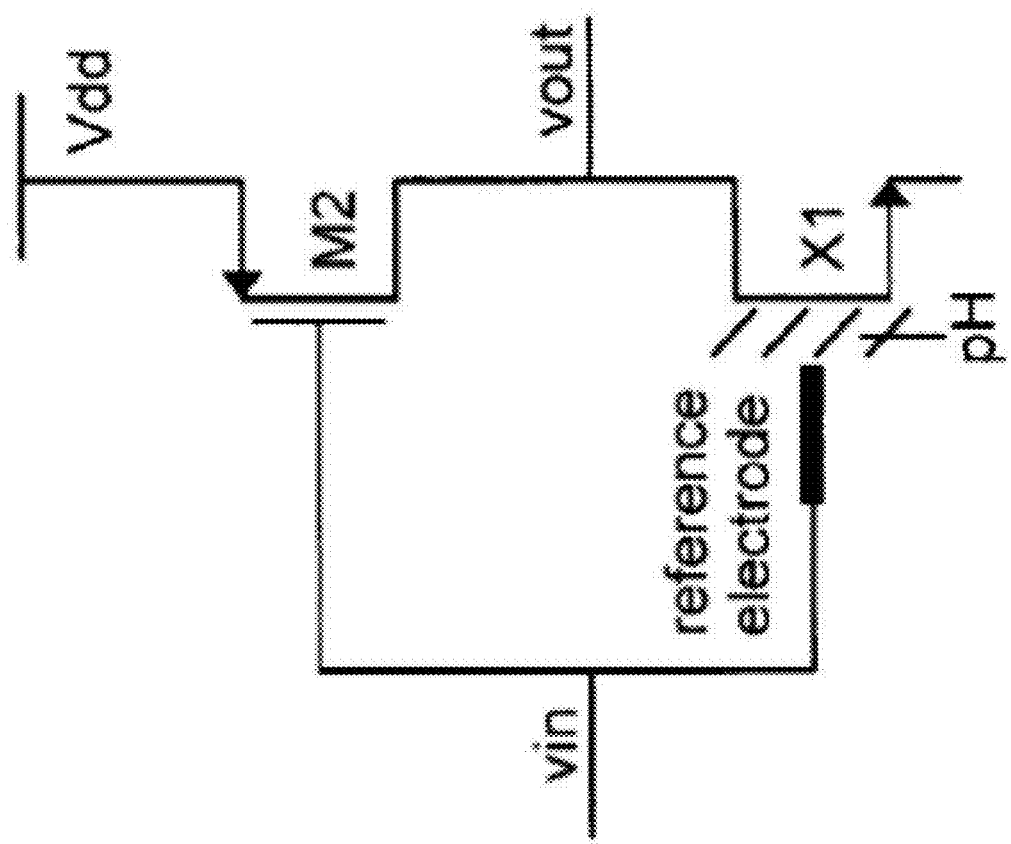
FIG. 4 is a prior art ISFET inverter.
Figure 5:
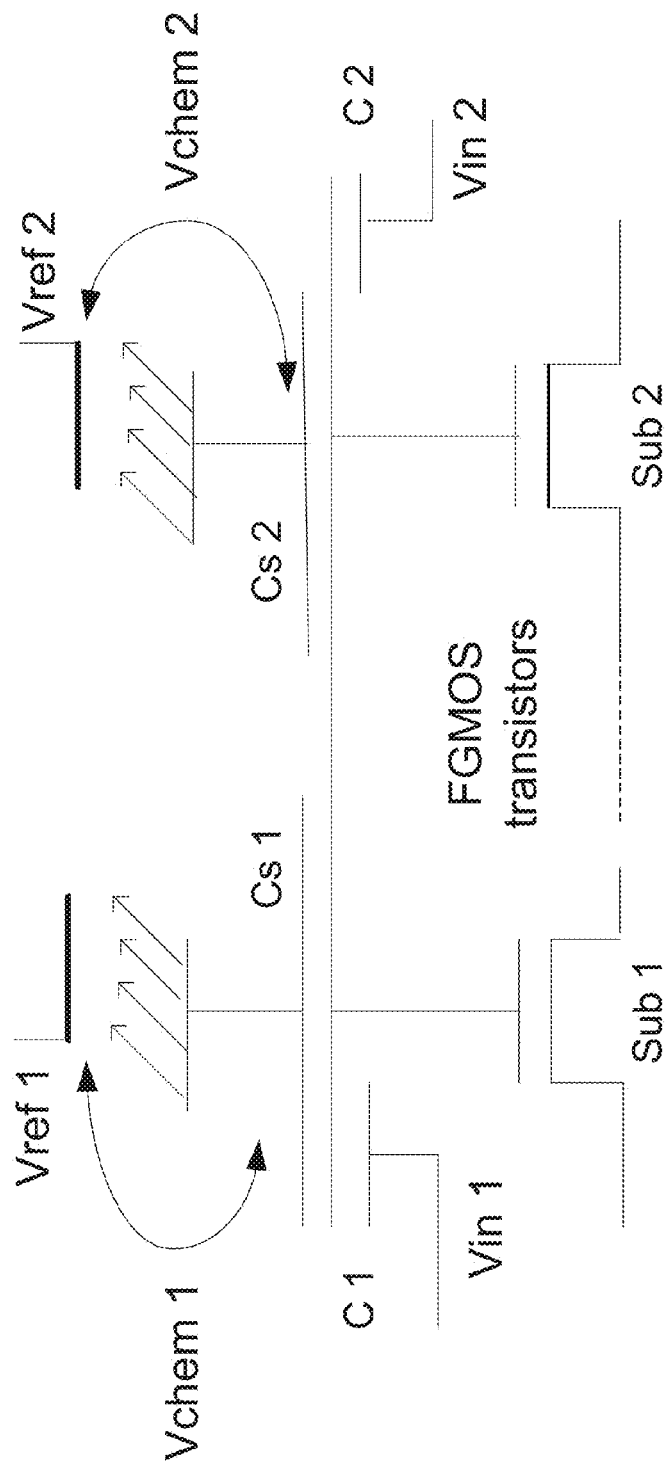
FIG. 5 is an illustration of a generalised ion sensitive device with multiple inputs.

Since a number of inputs can be capacitively coupled to the floating gate and its potential is defined by the weighted sum of the input gates' voltages (13). Therefore, the ISFET of FIG. 5 is a FG-MOS with only one input that is the superposition of Vref and Vchem being capacitively coupled by the passivation ion sensitive layer. Its floating gate voltage (Vfg) is given by:

$$V_{fg} = \frac{(V_{ref} + V_{chem}) * C_{pass} + V_{GD}C_{GD} + V_{GS}C_{GS} + V_{GB}C_{GB}}{C_{tot}} \quad (7)$$

Where $C_{pass}$ is the passivation capacitance, $C_{tot}$ is the total capacitance seen by the floating gate (15). And $V_{GD}$, $V_{GS}$, $V_{GB}$, $C_{GD}$, $C_{GS}$, $C_{GB}$ are the transistors gate-drain, gate-source, and gate-bulk voltages and capacitances consecutively. The factor $C_{pass}/C_{tot}$ scales down the effect of $V_{chem}$ and hence pH sensitivity. However, it can be made close to unity by maximizing ($C_{pass}/C_{tot}$) ratio that is by designing the chemical gate much larger than the electrical gate. This is one reason for the known sub-Nernstian sensitivity of ISFETs built with standard CMOS processes.

Figure 6:
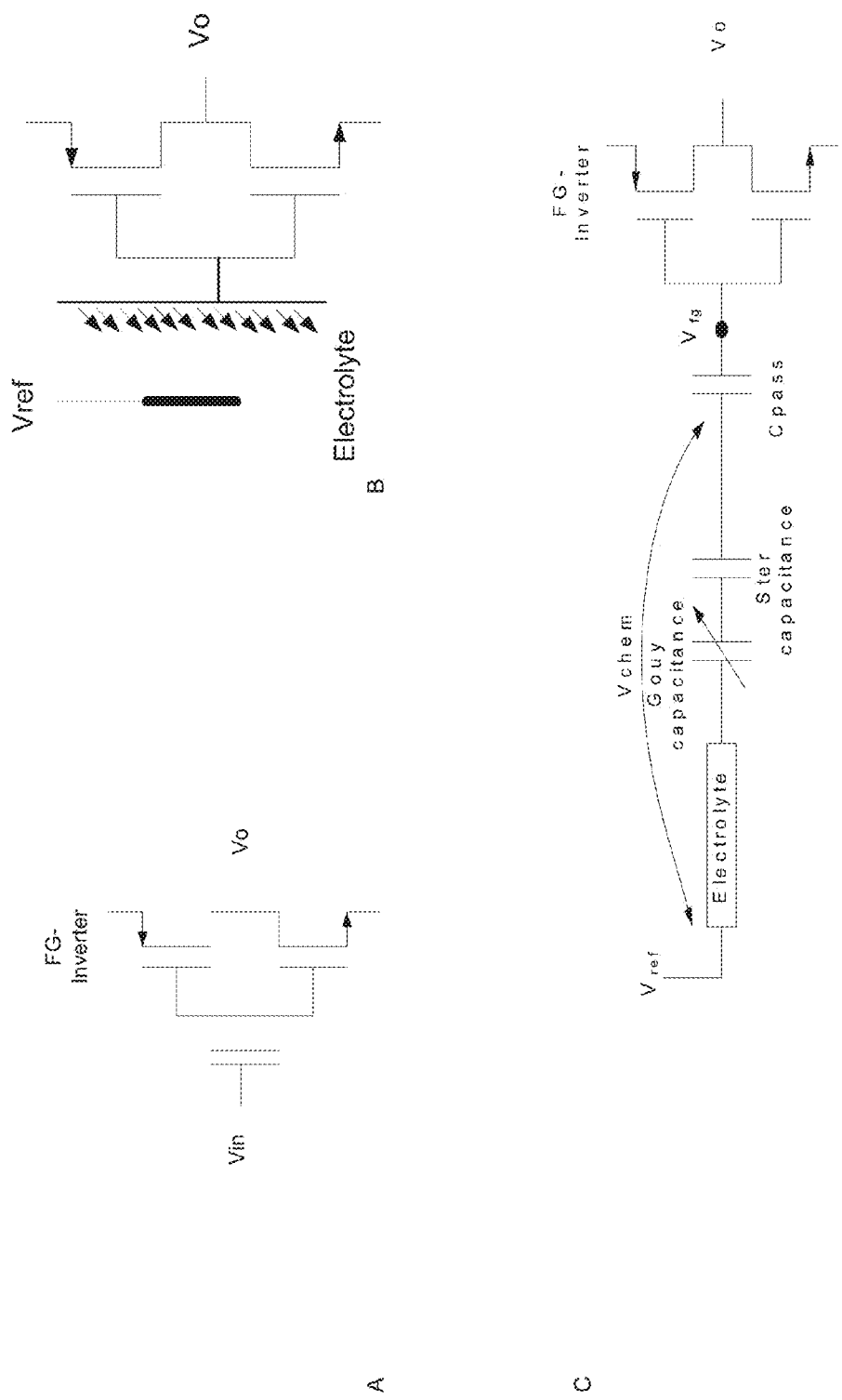
FIG. 6 is a (A) Schematic representation of an FGMOS, (B) Schematic representation of an ISFET inverter, (C) equivalent circuit of the ISFET inverter.

A standard FG inverter is composed of floating gate NMOS and PMOS transistors in a standard class AB inverting amplifier as shown schematically in FIG. 6-A. The single input of this inverter is capacitively coupled to the two floating gates.

In embodiments of the invention a plurality of ISFETs share the same ion sensing membrane and floating gate. In a preferred embodiment providing an inverter, two ISFETs, one NMOS and one PMOS, are arranged as shown in FIG. 6-B. FIG. 6-C is an equivalent circuit schematic for such an inverter.

This circuit can be used to perform reaction monitoring and pH-thresholding operations for a reaction chamber. It can be used to process signals from an array of ISFETs exposed to an array of reaction chambers. Each chamber is placed on top of an ISFET-pair inverter with either a global or local $V_{ref}$. Each pixel of the array gives a digital output that can be latched or digitally processed in the same IC without the need for Analogue to Digital conversion. This facilitates the construction of completely digital ISFET-based lab-on-chip applications.

Figure 7:
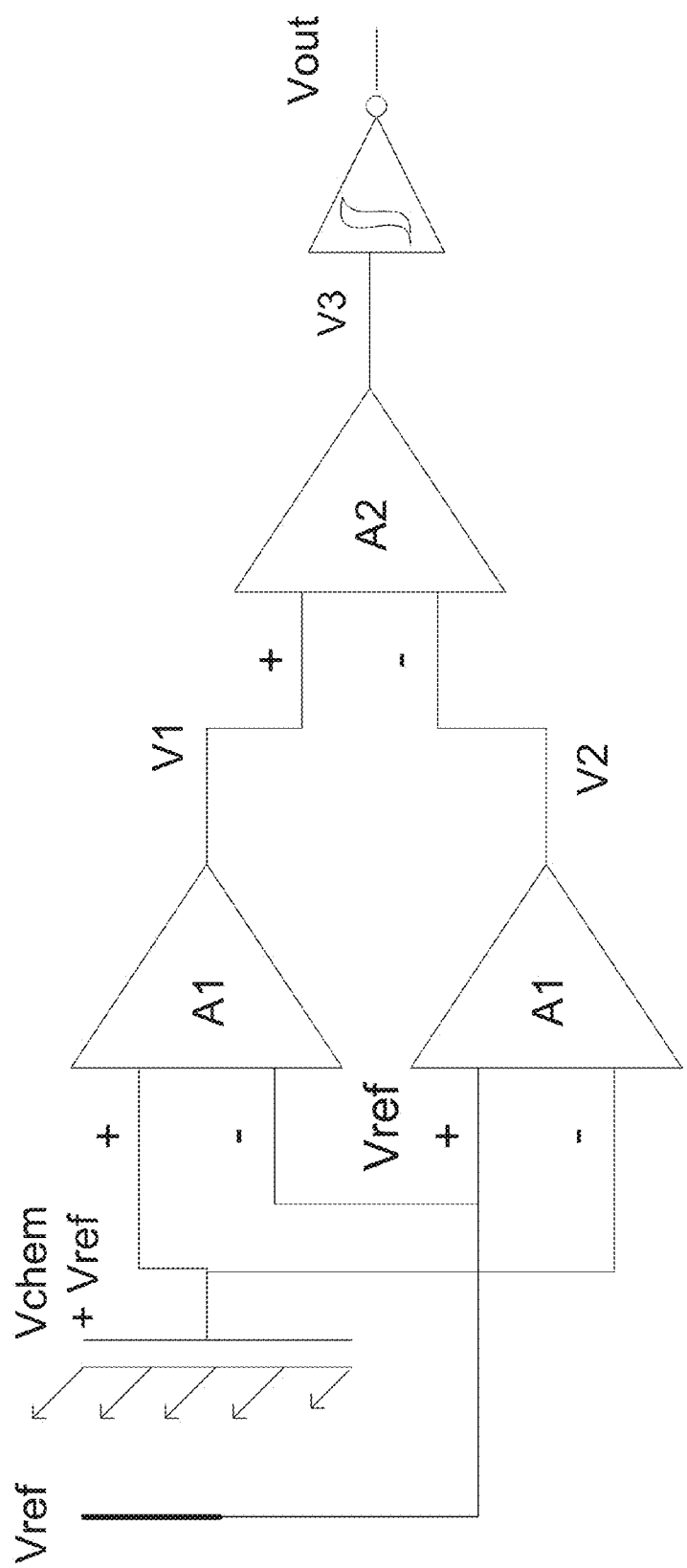
FIG. 7 is a circuit representation of an amplified chemical inverter.
Figure 8:
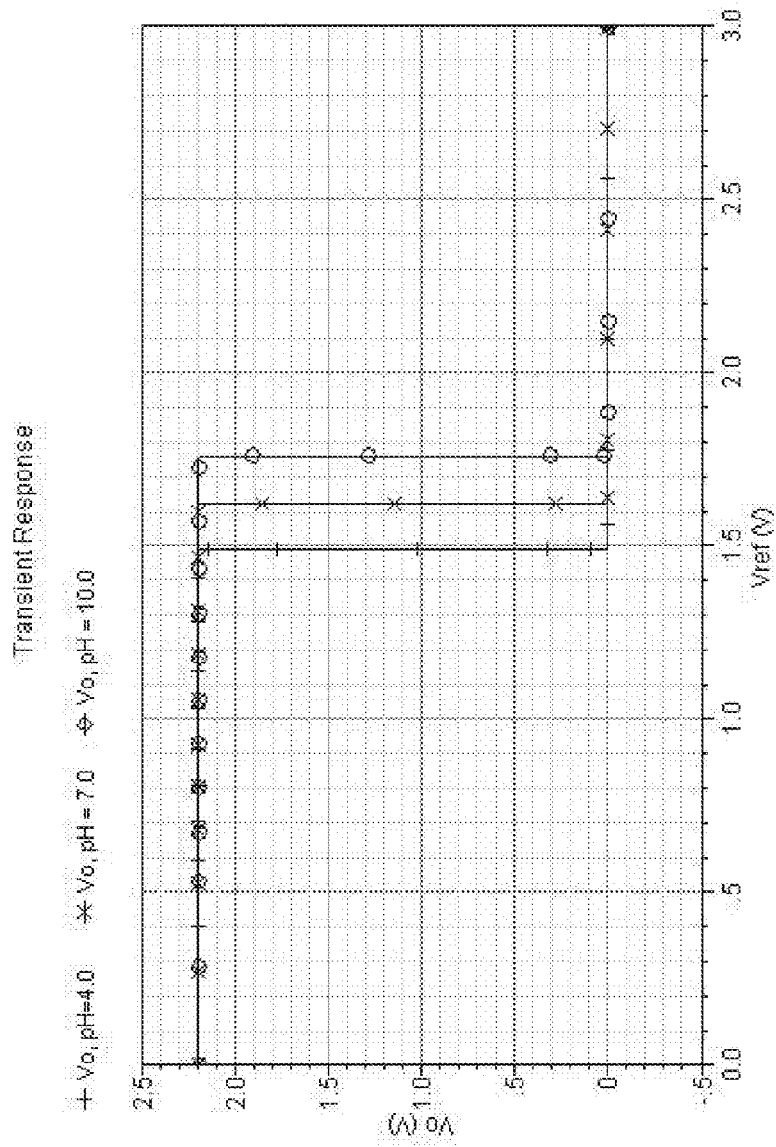
FIG. 8 is a graph showing the switching point for an ISFET inverter.
Figure 9:
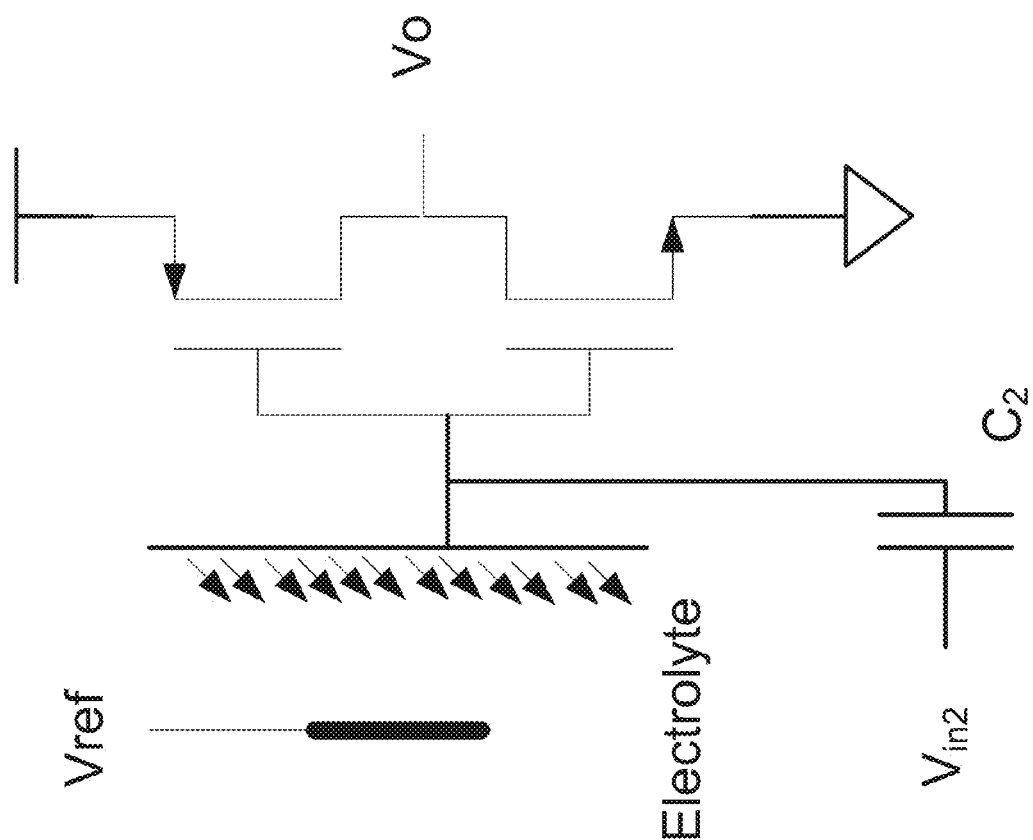
FIG. 9 shows an ISFET inverter with a second input.
Figure 10:
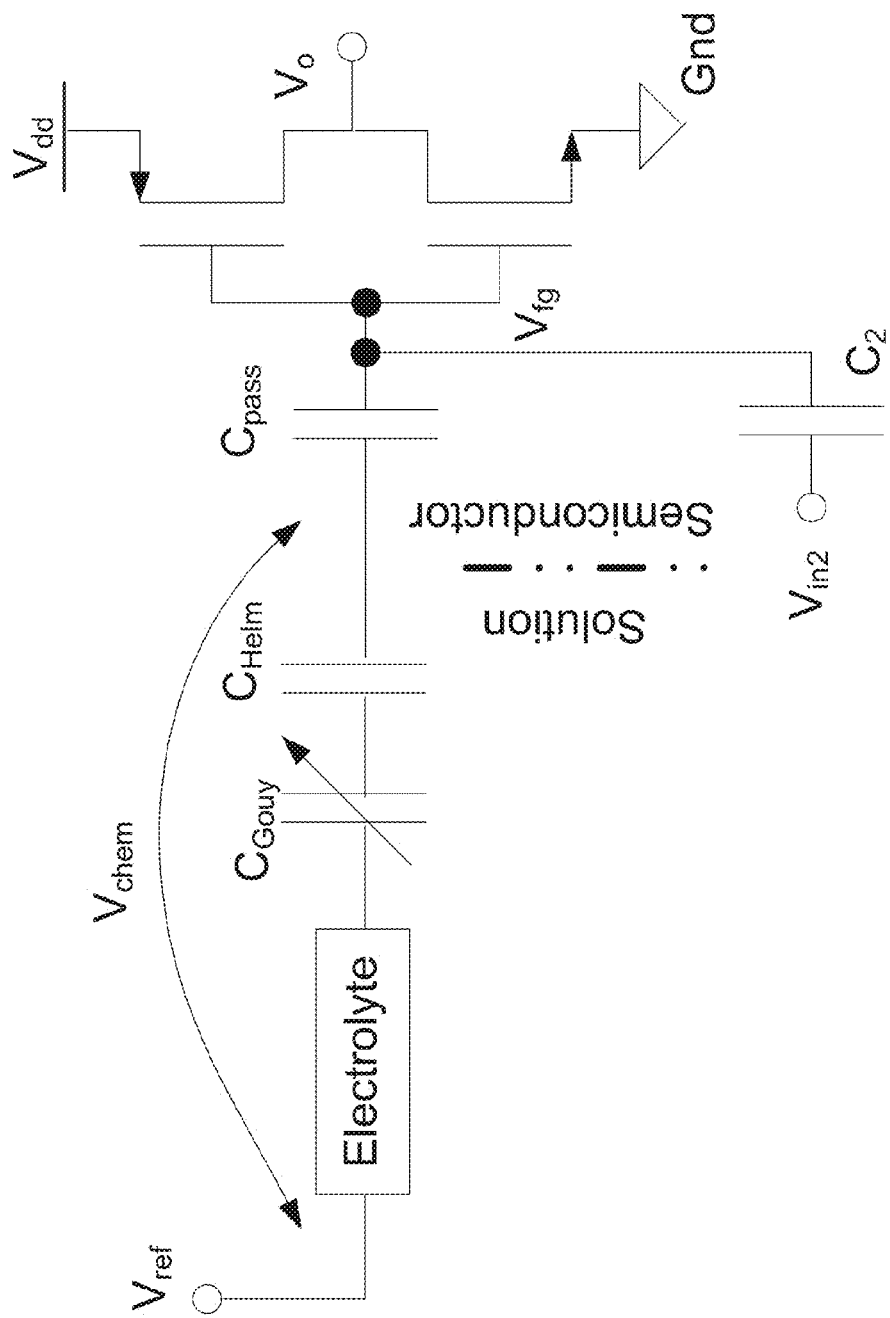
FIG. 10 is a model of enhanced sensitivity ISFET based chemical inverter.
Figure 11:
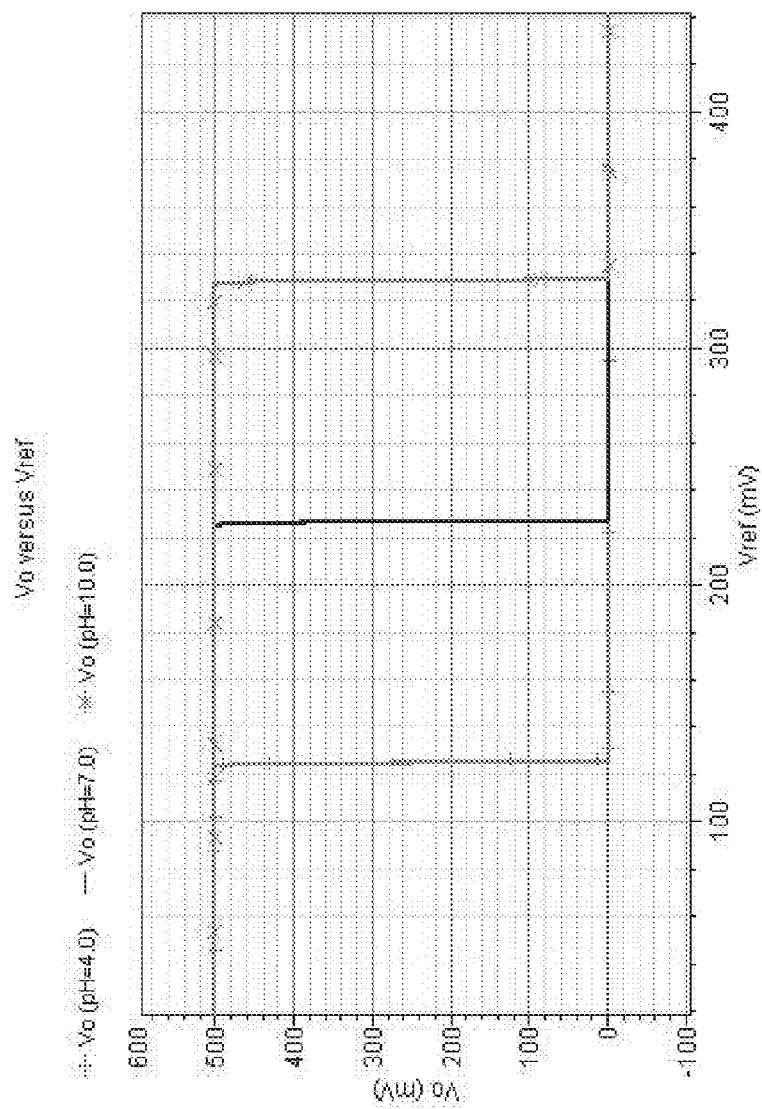
FIG. 11 is a graph showing the output of Vref sweeps for circuit of FIG. 10 with constant second input Vin2.

To enhance pH sensitivity, an amplifier may be used to amplify $V_{chem}$, which is effectively the difference between the floating gate and the reference electrode immersed in the electrolyte under test. The circuit in FIG. 7 is a possible realization. The voltage [$V_3 = 2 A_1 A_2 V_{chem}$] is an amplified version of the voltage across the ISCAP which reflects the electrolyte pH. Its output is fed to a Schmitt Trigger circuit. The output ($V_{out}$) is a digital signal that switches state when the solution's pH undergoes a change greater than a threshold value.

Results:

In the ISFET of FIG. 6-B, the input is supplied to the floating gate of a single transistor amplifier. Depending on the region of operation, it follows one of the $I_d$-$V_{gs}$ relations of equation (1). Normally either $I_d$ or $V_{ds}$ is made constant while the other represents the output.

For the inverter of FIG. 6-C, in order to find the switching threshold voltage, its circuit is split into two parts: the input part that is used to find $V_{fg}$ which is the input to the second part: the standard inverter. By charge conservation $V_{fg}$ is given by:

$$V_{fg} = \frac{C_{pass}}{C_{tot}}(V_{chem} + V_{ref}) + \frac{VC_{nMOS} + VC_{pMOS}}{C_{tot}} \quad (8)$$

Where:
($VC_{xMOS} = V_{GDx}C_{GDx} + V_{GSx}C_{GSx} + V_{GBx}C_{GBx}$) and (x) is (n) for n-MOS and (p) for p-MOS.

For the standard inverter, the switching threshold voltage ($V_{sth}$) is the point when the input floating gate voltage ($V_{fg}$) equals the output ($V_0$). Thus both transistors are in saturation as $V_{gs} = V_{ds}$. It is found by equating the currents through both transistors and solving for this point. It was found in (18)-p. 186 to be:

$$V_{sth} = \frac{V_{tn} + r(V_{dd} + V_{tp})}{1 + r}; \text{Where } r = \sqrt{\frac{-k_p}{k_n}} \quad (9)$$

Where, $V_{tn}$ and $V_{tp}$ are threshold voltages while $k_n$ and $k_p$ are {mobility ($\mu$)×gate oxide capacitance ($C_{ox}$)} for NMOS and PMOS respectively. This is for strong inversion and low $V_{dd}$ such that both transistors do not reach velocity saturation (18). Therefore, switching takes place when $V_{fg} = V_{sth}$, which gives:

$$(V_{chem} + V_{ref}) = \frac{C_{tot}}{C_{pass}}V_{sth} - \frac{VC_{nMOS} + VC_{pMOS}}{C_{pass}} \quad (10)$$

Switching is triggered by the sum of $V_{chem}$ and $V_{ref}$. The first term is pH dependent, as in equation (5). It includes $V_{Qpass}$ which manifests itself as a shift in the switching point.

$V_{ref}$ is decided by the user and it is analogous to $V_{in}$ of the FG inverter, keeping in mind the difference in coupling capacitance. $V_{chem}$ has the effect of shifting the switching threshold voltage if $V_{ref}$ is the input. By the same way, if $V_{chem}$ is the input $V_{ref}$ will shift the switching point.

Results

An exemplary embodiment of the device is discussed below including results of its use in an exemplary embodiment of the method.

The transistors had a length of 0.35 µm but their widths were 4 µm and 12 µm for the n and p devices respectively. In Figure, $V_{ref}$ was swept for the ISFET and the switching point was found for pH values of 4.0, 7.0, and 10.0. The switching points were 1.49V, 1.63V, and 1.76V respectively. This gives a sensitivity of 44.52 mV/pH. $V_{dd}$ of 2.2V was used.

The output was buffered by two MOS inverters increasing in size in order to provide enough current to drive the load introduced by the bond-pad and test PCB. The chemical sensitive area was 35×200 µm². A single junction Ag/AgCl glass reference electrode was immersed in the electrolyte under test in order to apply $V_{ref}$. It was chosen because of its stable junction voltage. Three different pH buffer solutions (4.0, 7.0, and 10.0) were tested.

The reference voltage was swept for each case in order to find the value that caused switching for different pH values. The sensitivity, measured as the switching voltage shift, was found to be 28.33 mV/pH.

The switching operation may be driven by pH change alone. $V_{ref}$ may be fixed close to the switching point of the current pH. This is the initial condition of logic "1". If the solution's pH is changed by titrating 0.1M HCl to lower the pH to 6.5±0.1. This gave logic "0". Then, 0.1M NaOH can be titrated in order to bring the pH back to 7.0±0.1. Embodiments of the third aspect of the invention provide a second input to the floating gate of the ISFET, as shown in Figure. This arrangement provides the inverter with two inputs: the ion sensitive input coupled through passivation capacitance and the second input (Vin2) coupled through capacitance ($C_2$). The resultant floating gate voltage is the weighted sum of these two inputs.

By making the second input's capacitance ($C_2$) very small compared to passivation capacitance ($C_{pass}$), it is possible to use this input ($V_{in2}$) as the electrical inverter input while the chemical signal is used as a control gate. Thus, the switching point referred to *$V_{in2}$ becomes very sensitive to pH changes. In fact, it is a scaled version of the pH sensitivity referenced to $V_{ref}$. The scaling factor is the ratio $C_{pass}/C_2$. The choice of this ratio is application dependent and is preferably greater than 10, more preferably greater than 50, 100, 500 or 1000.

Since a number of nodes are capacitively coupled to the floating gate, its potential is defined by the weighted sum of the inputs. The floating gate voltage ($V_{fg}$) is given by:

$$V_{fg} = \frac{C_{pass}}{C_{tot}}(V_{chem} + V_{ref}) + \frac{C_2}{C_{tot}}V_{in3} + \frac{VC_{nMOS} + VC_{pMOS}}{C_{tot}} \quad (11)$$

Where:

$$(VC_{nMOS} = V_{Dn}C_{GDn} + V_{Sn}C_{GSn} + V_{Bn}C_{GBn})$$

and $$(VC_{pMOS} = V_{Dp}C_{GDp} + V_{Sp}C_{GSp} + V_{Bp}C_{GBp})$$

Here, $VC_{nMOS}$ is the nMOS's contribution to the floating gate voltage. That is its drain voltage ($V_{Dn}$) multiplied by its gate drain capacitance ($C_{GDn}$), its source voltage ($V_{Sn}$) multiplied by its gate source capacitance ($C_{GSn}$), and its body voltage ($V_{Bn}$) multiplied by gate body capacitance ($C_{GBn}$). All voltages refer to ground. The suffix (n) stands for nMOS. $VC_{pMOS}$ is the pMOS's contribution to the floating gate voltage. It is calculated in a similar way. $C_{pass}$ is the passivation capacitance, $V_{chem}$ is the pH dependent chemical voltage given by equation 11. $V_{ref}$ is the reference electrode voltage, and $C_{tot}$ is the total capacitance seen by the floating gate. It includes all other parasitic capacitances not dealt with separately here.

It is customary to assume that the floating gate has no charges and thus have zero initial voltage. However, this may not be the case in real life where they manifest themselves as a shift in the initial voltage of the floating gate.

From equation 11, the factor $C_{pass}/C_{tot}$ scales down the effect of $V_{chem}$ and hence pH sensitivity. However, it can be made close to unity by maximizing ($C_{pass}/C_{tot}$) ratio. That is by designing the passivation capacitance much larger than the sum of all other capacitances in the circuit. This is one reason for sub-Nernstian sensitivity of ISFETs built with standard CMOS processes. The second term of equation (11) is the second input scaled down by $C_2/C_{pass}$. The reciprocal of this ratio is the amplification of pH sensitivity referred to Vin2. Thus, its choice should consider application requirements and in the same time minimizing $C_2$ to allow more room for chemical sensitivity.

An inverter operating in weak inversion has its switching threshold voltage ($V_{sth}$) when both transistors have the same current:

$$V_{sth} = \frac{V_{dd} - |V_{tp}| + \ln\left(\frac{I_{sn}}{I_{sp}}\right)V_{tn}}{1 + \ln\left(\frac{I_{sn}}{I_{sp}}\right)} \quad (12)$$

$V_{tn}$ and $V_{tp}$ are the threshold voltages while $I_{sn}$ and $I_{sp}$ are the source currents of the NMOS and PMOS transistors respectively. $V_{dd}$ is the supply voltage.

This switching threshold voltage of equation (3) depends only on MOS parameters. Switching occurs when $V_{fg}$ changes crossing $V_{sth}$ going higher or lower than it.

Since the floating gate voltage is a function of its coupled voltages as in equation (1) these inputs affect its switching point. Thus, defining its pH sensitivity is not as straight forward as the single ISFET case. It can be defined as the pH induced shift in $V_{fg}$. But, this is difficult to measure as there is no direct access to it. But it is possible to refer it to one of its inputs namely: $V_{ref}$, or Vin2. Therefore, pH sensitivity is manifested as the shift in the switching voltage, due to pH change, as seen by sweeping either of one of them while keeping the other constant.

The sensitivity of floating gate of this inverter for pH referred to $V_{ref}$ while $V_{in2}$ is constant is found by:

$$V_{fg} \text{ sensitivity to pH} \frac{dV_{fg}}{d\text{pH}} = \frac{C_{pass}}{C_{tot}} 2.3\alpha U_T V/\text{pH} \quad (13)$$

-continued $$V_{fg} \text{ sensitivity to } V_{ref} = \frac{dV_{fg}}{dV_{ref}} = \frac{C_{pass}}{C_{tot}} \text{ Thus,} \quad (14)$$

$V_{fg}$ sensitivity to pH, (15)

$$\text{referenced to } Vref = \frac{dV_{fg}}{d\text{pH}} \times \frac{dV_{ref}}{dV_{fg}} = \frac{dV_{ref}}{d\text{pH}} = 2.3\alpha U_T / V / \text{pH}$$

Therefore, despite the fact that the effect of $V_{ref}$ on $V_{fg}$ is scaled down by the ratio $C_{pass}/C_{tot}$, the pH sensitivity when referred to $V_{ref}$ is not, as $V_{chem}$ itself is scaled down by the same ratio. The scaling cancels out.

However, if Vin2 is used to shift $V_{fg}$ while the $V_{ref}$ is fixed, then:

$$V_{fg} \text{ sensitivity for } V_{in2} = \frac{dV_{fg}}{dV_{in2}} = \frac{C_2}{C_{tot}} \quad (16)$$

$$V_{fg} \text{ sensitivity to pH, referenced to } V_{in3} = \quad (17)$$

$$\frac{dV_{fg}}{d\text{pH}} \times \frac{dV_{in2}}{dV_{fg}} = \frac{dV_{in2}}{d\text{pH}} = \frac{C_{pass}}{C_2} 2.3\alpha U_T V / \text{pH}$$

Therefore, if Vin2 is used as the input where $V_{ref}$ is constant and the chemical gate plays the role of a control gate that shifts the switching point, then the circuit's pH sensitivity with reference to Vin2 is scaled up by $C_{pass}/C_2$.

It is possible, by design, to make $C_{pass}=AC_2$. Then pH sensitivity is scaled up by the ratio A without the need for any type of amplifier. Thus by using Vin2 as the inverter's electrical input, the coupling weight is used to enhance the pH sensitivity.

The skilled person in the art will choose this amplification ratio according to their application in such a way that when Vin2 is swept through its full range, it will correspond to observable pH values. For example, if the expected pH change spans two pH units, e.g. from pH 6 to pH 8; and Vin2 is allowed to span the values from 0 to 1V and the expected pH sensitivity referenced to $V_{ref}$ is 30 mV/pH, then a value of $C_{pass}/C_2=A=1V/30 mV/2 \approx 16$. $V_{ref}$ should be chosen in such a way to set the output of the circuit with the desired initial logic and wither the inverter at the verge of switching. This will allow pH changes to be easily detectable by Vin2.

For example, in an exemplary embodiment the threshold voltage of the N-MOS device is 0.59V and the PMOS device's threshold voltage is –0.72V. Therefore, using $V_{dd}$ of 0.5V insures sub-threshold operation by capping the maximum voltage a transistor sees to less than its threshold voltage.

$V_{ref}$ can then be swept to find a value that causes switching ($V_{ref,sth}$). The pH of the electrolyte was stepped from pH4.0 to pH7.0 to pH10.0. Vin2 was set to zero volts.

The output is shown in Figure. The simulated sensitivity is thus:

$$\frac{\Delta V_{ref,sth}}{\Delta \text{pH}} = 33.9 \text{ mV/pH}.$$

$C_{pass}=420$ fF and $C_2=3$ fF which gives a scaling factor of $C_{pass}/C_2=140$. Thus the pH sensitivity with respect to Vin2 is $\{(C_{pass}/C_2) \times 0.0339\}=4.7$V/pH. $V_{ref}$ is kept constant at the verge of switching while Vin2 is swept to find the switching point ($Vin2_{sth}$) for pH values.

While the inverter arrangement can be used to detect a 0.1 pH change, the additional Vin2 signal coupled to the floating gate by an arbitrarily large scaling factor can detect an even smaller change, for example 0.001.

The high sensitivity is not attained by improving the ISFET's physical sensitivity. Instead pH sensitivity can thus be made very high by exploiting the floating gate nature of the ISFET built in unmodified CMOS process. Whilst similar results are attainable using an amplifier, this comes with extra costs of area, power and noise. The advantage here is the high gain without these associated problems.

This circuit can serve as the basic building block for an array of pH switches, forming pixels. They are capable of providing digital output from chemical or biological inputs. With feedback to the reference electrode, it is possible to change the switching threshold voltage to reflect the needed pH region of interest.

Preferably the sensing layer is exposed to a chamber having a concentration of a target ion. The ion concentration may be constant such that the output signals of the ISFET switch will be constant. The ion concentration may vary in time or as the result of a chemical reaction such that the output signals of the ISFET switch will detect a change in the ion concentration.

Preferably the chemical reaction is the incorporation of a nucleotide onto a nucleic acid such that protons are released. The nucleic acid may be unknown and the nucleotide reagents known such that the output of the circuit indicates a change (of lack thereof) in pH was observed due to the nucleotide reagents being complementary (or not) to the unknown nucleic acid.

Figure 12:
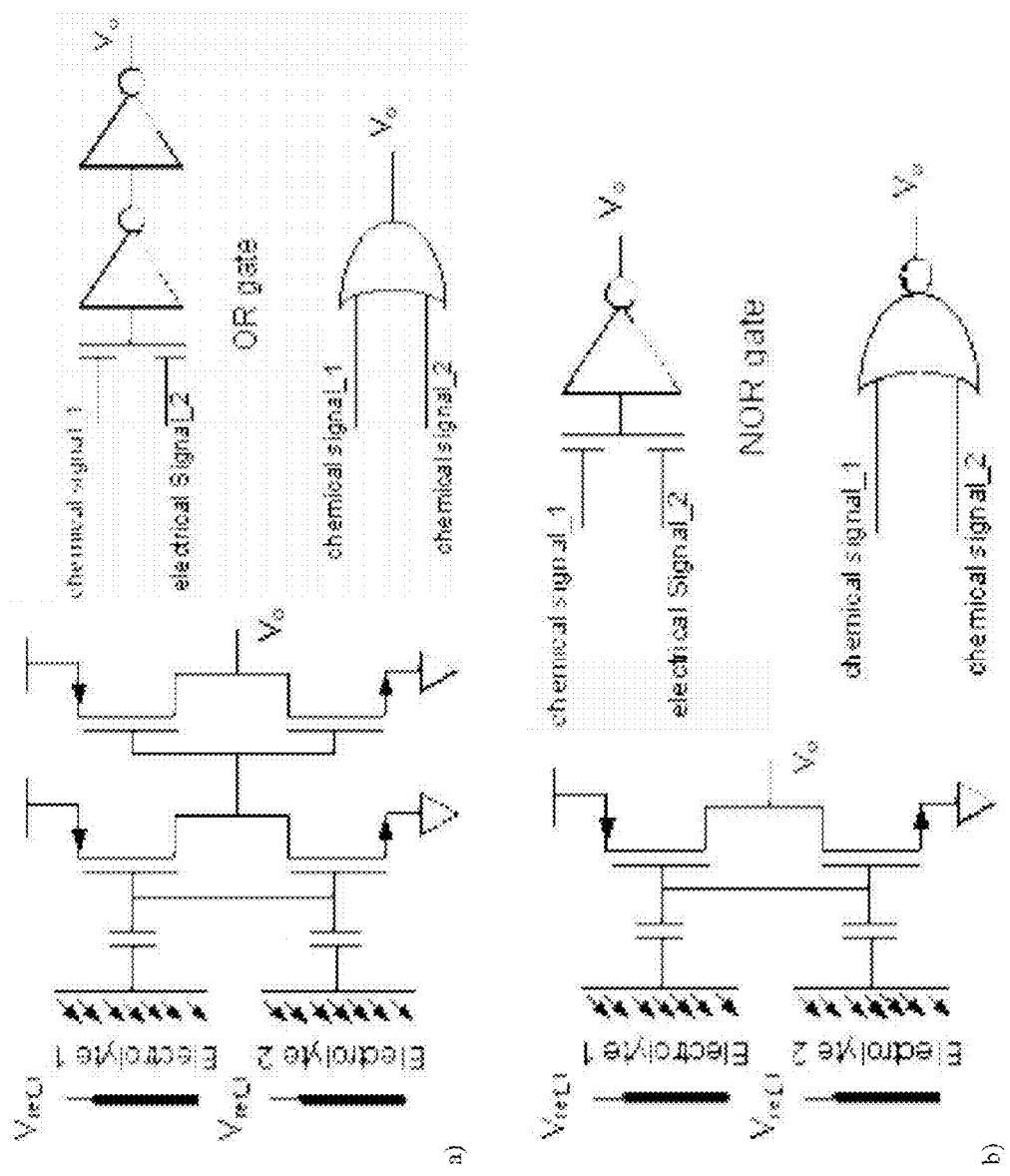
FIG. 12 is a circuit diagrams of a) an AND gate and b) an OR gate.

In some embodiments, there is a plurality of chambers, each of which is exposed to devices of the invention to detect a concentration of a target ion, or detectect a change in a concentration of a target ion. The outputs of the devices can be connected to perform logic operations such as AND, NAND, OR, NOR, XOR, XNOR, and their combinations. The skilled person will appreciate how this may be accomplished. Exemplary circuit are shown in FIG. 12.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

REFERENCES

1—P. Bergveld, "Thirty years of ISFETOLOGY What happened in the past 30 years and what may happen in the next 30 years", Sensors and Actuators, V 88, pp. 1-20, 2003.
2—Leila Shepherd, Pantelis Georgiou, and Chris Toumazou, "A novel voltage clamped CMOS ISFET sensor interface", IEEE International Symposium on Circuits and Systems ISCAS, pp. 3331-3334, 2007.
3—Christofer Toumazou, Bhusana Premanode, Leila Shepherd; U.S. Patent No. 2010/0159461 A1, "Ion Sensitive Field Effect Transistors", Pub. Date: Jun. 24, 2010.
4—Tadayuki Matsuo and Masayoshi Esashi, "Methods of ISFET Fabrication", Sensors and Actuators, Vol. 1, pp. 77-96, 1981.

5—J. Bausells, J. Carrabina, A. Errachid, A. Merlos, "Ion-sensitive field-effect transistors fabricated in a commercial CMOS technology", Sensors and Actuators B 57, pp. 56-62, 1999.

6—P. A. Hammond, D. Ali, D. R. S. Cumming, "A Single-Chip pH Sensor Fabricated by a Conventional CMOS Process", Proceedings of IEEE Sensors, Vol. 1, pp. 350-355, 2002.

7—Winston Wong, Leila Shepherd, Pantelis Georgiou and Chris Toumazou, "Towards ISFET based DNA Logic for Rapid nucleic acid detection", IEEE Sensors conference pp. 1451-1454, 2009.

8—Tadashi Shabata, and Tadahiro Ohmi, "A Functional MOS Transistor Featuring Gate-Level Weighted Sum and Threshold Operations", IEEE Transactions on Electron Devices, Vol. 39, No. 6, pp. 1444-1455, 1992.

9—P. Georgiou and C. Toumazou, "CMOS Based Programmable ISFET", Electronic Letters, Vol. 44 No. 22, 2008, pp. 1289-1290.

10-W. Wong Jr, P. Georgiou, C.-P. Ou, and C. Toumazou, "PG-ISFET based DNA-logic for reaction monitoring", Electronics Letters, Vol. 46, No. 5, 2010, pp. 330-332.

11—Prakash, S. B.; Abshire, P.; "A CMOS capacitance sensor that monitors cell viability", IEEE Sensors Conference 2005, pp. 1177-1180.

12—Shibata, T.; Kosaka, H.; Ishii, H.; Ohmi, T.; "A neuron-MOS neural network using self-learning-compatible synapse circuits", IEEE Journal of Solid-State Circuits, Volume: 30, Issue 8, pp. 913-922, 1995.

13—Jayant, K.; Porri, T.; Erickson, J. W.; Kan, E. C.; "Label-free electronic detection of growth factor induced cellular chatter on chemoreceptive neuron MOS (CvMOS) transistors", International Conference on Solid-State Sensors, Actuators and Microsystems, pp. 1814-1817, 2009.

14—Themistoklis Prodromakis, Yan Liu, Timothy Constandinou, Pantelis Georgiou, Chris Toumazou, "Exploiting CMOS Technology to Enhance the Performance of ISFET Sensors", IEEE Electron Device Letters, Vol. 31, NO. 9, pp. 1053-1055, 2010.

15—Sunil Purushothaman, Chris Toumazou, and Chung-Pei Ou, "Proton and Single nucleotide polymorphism detection: A simple use for the Ion Sensitive Field Effect Transistor", Sensors and Actuators, B 114, pp. 964-968, 2006.

16—Qintao Zhang, Vivek Subramanian, "DNA hybridisation detection with organic thin film transistors: Toward Fast Disposable DNA microarray chip", Biosensors and Bioelectronics, Vol. 22, pp. 3182-3187, 2007.

17—S. Purushothaman, C. Toumazou, and J. Georgiou, "Towards Fast Solid State DNA Sequencing", IEEE International Sumposium on Circuits and Systems, pp. IV-169-IV-172, 2002.

18—P. Georgiou and C. Toumazou, "CMOS Programmable Gate ISFET", Electronics letters, Vol. 44, pp. 1289-1290, 2008.

19—Liu Yan, Pantelis Georgiou, Timothy G. Constandinou, David Garner and Chris Toumazou, "An Auto-Offset-Removal circuit for chemical sensing based on the PG-ISFET", IEEE International Symposioum on Circuits and Systems, ISCAS 2009, pp. 1165-1168.

20—Austriamicrosystems, "0.35 μm CMOS C35 Process Parameters", Document Number: ENG-182, revision#: 6.0, 12.12.2008.

21—Mark J. Milgrew; and David R. S. Cumming, "Matching the Transconductance Characteristics of CMOS ISFET Arrays by Removing Trapped Charge", IEEE Transaction of Electron Devices, Vol. 55, No. 4, pp. 1074-1079, 2008.

22—Jan, M. Rabaey, Anantha Chandrakasan, and Borivoje Nikolic, "Digital Integrated Circuits", Prentice Hall, second edition, 2003.*

The invention claimed is:

1. A semiconductor device for detecting a change in ion concentration of a sample, the device comprising:
a plurality of Field Effect Transistors (FETs) coupled to a common floating gate; and an ion sensing layer exposed to the sample and coupled to the floating gate;
a circuit comprising the plurality of FETs to provide a digital output whose state depends on the ion concentration of the sample; and
one or more first electrical input signals coupled to the floating gate for removing or adding a charge to the floating gate to set a switching threshold for the plurality of transistors.

2. The device of claim 1,
wherein, in use, a current through the transistors is switched on or off depending on the magnitude of the ion concentration in the sample in proximity to the sensing layer compared to a switching threshold.

3. The device of claim 2, wherein the semiconductor device is used with a circuit.

4. A semiconductor device for detecting a change in ion concentration of a sample, according to claim 3, wherein the circuit comprises a plurality of devices that are connected together to implement logic functions selected from one of: AND, NAND, OR, NOR, XOR, XNOR, and their combinations.

5. The device of claim 1, further comprising a reference electrode on the semiconductor device exposed to the sample.

6. The device of claim 5, wherein an input voltage coupled to the reference electrode is arranged to set a switching threshold of the plurality of FETs.

7. A device according to claim 1, wherein the plurality of FETs comprise a P type FET and an N type FET arranged in a comparator configuration.

8. A device according to claim 1, wherein the plurality of FETs comprise a P type FET and an N type FET arranged in an inverter configuration.

9. A device according to claim 1, wherein the plurality of FETs comprise a P type FET and an N type FET are arranged in an inverter configuration having an output signal is an output of logic one or logic zero according to an ion concentration of the sample.

10. A device according to claim 1, wherein the FETs are biased in weak inversion.

11. A device according to claim 1, wherein the FETs are biased in such a way to switch between saturation and cut-off.

12. A device according to claim 1, wherein the one or more first electrical input signals is arranged to be coupled to the floating gate to set the switching threshold and de-coupled when not setting the switching threshold.

13. A device according to claim 1, wherein said one or more first electrical input signals comprise one signal connected to a positive voltage and one signal connected to a negative voltage.

14. A device according to claim 1, further comprising a second electrical input signal coupled to the floating gate, wherein the second electrical input signal is arranged to change in magnitude so as to switch the plurality of Field Effect Transistors.

15. A device according to claim 14, wherein the ion sensing layer is coupled to the floating gate by a first capacitance and wherein the second electrical input signal is coupled to the floating gate by a second capacitance.

16. A device according to claim 15, wherein a ratio of first capacitance to second capacitance is more than 1.

17. The device of claim 1, further comprising: at least one reaction chamber for each of a plurality of chemical reactions, which chemical reactions change an ion concentration in the reaction chamber;

wherein each reaction chamber is provided with a device-associated with the plurality of Field Effect Transistors (FETs) coupled to a common floating gate, each device providing a digital output signal whose state depends on the ion concentration of a sample in that chamber, and wherein the outputs are coupled together to form a digital signal processing circuit for evaluating a logical function.

18. A method of providing an output representing a concentration of a target ion in a sample, the method comprising:

providing a CMOS switch comprising a plurality of Field Effect Transistors (FETs) coupled to a common floating gate and an ion sensing layer exposed to the sample and coupled to the floating gate;

exposing the ion sensitive layer to the sample to switch a state of the CMOS switch on or off;

outputting a signal from the CMOS switch; and setting a voltage of a first electrical input signal coupled to the floating gate to set a charge on the floating gate, which charge is zero volts.

19. A method according to claim 18, further comprising exposing a reference electrode to the sample to bias the plurality of FETs to set a switching threshold of the CMOS switch.

20. A method according to claim 19, further comprising varying a reference voltage to determine the current ion concentration and then setting the reference voltage such that the CMOS switch will switch state if the ion concentration changes by more than a predetermined amount.

21. A method according to claim 18, further comprising setting a reference voltage connected to a reference electrode to set a switching threshold of the CMOS switch corresponding to a predetermined ion concentration.

22. A method according to claim 18, further comprising varying a voltage of a second electrical input coupled to the floating gate to switch the state of the CMOS switch.

23. A method according to claim 18, wherein the output signal is a digital signal.

24. A method according to claim 18, further comprising starting a chemical reaction whose product comprises the target ion.

* * * * *